United States Patent [19]
Bussey et al.

[11] Patent Number: 6,153,376
[45] Date of Patent: Nov. 28, 2000

[54] **SCREENING USING *S. CEREVISIAE* MANNOSYLTRANSFERASE ENCODING GENES**

[75] Inventors: Howard Bussey, Westmount; Marc Lussier, Montréal; Anne-Marie Sdicu, Pierrefonds, all of Canada

[73] Assignee: McGill University, Montreal, Canada

[21] Appl. No.: 09/433,574

[22] Filed: Nov. 4, 1999

Related U.S. Application Data

[63] Continuation of application No. PCT/CA99/00227, Mar. 16, 1999.

[30] Foreign Application Priority Data

Mar. 19, 1998 [CA] Canada ................................ 2232536

[51] Int. Cl.$^7$ .............................. C12Q 1/00; C12Q 1/48; C12Q 1/02
[52] U.S. Cl. .................... 435/4; 435/15; 435/29
[58] Field of Search ................. 536/24.32, 23.1; 435/7.1, 7.31, 440, 4, 32

[56] References Cited

U.S. PATENT DOCUMENTS 5,194,600  3/1993  Bussey et al. .

FOREIGN PATENT DOCUMENTS 95 06132  3/1995  WIPO .
96 10082  4/1996  WIPO .
99 31269  6/1999  WIPO .

OTHER PUBLICATIONS

Lussier et al., Biochem.Biophys.Acta, vol. 1426, No. 2, pp. 323–334.
Lussier et al., Genetics, vol. 147, No. 2, pp. 435–450.
Lussier et al., J.Biol.Chem, vol. 272, No. 24, pp. 15527–15531.
Lussier et al., Yeast, vol. 13, No. 3, pp. 267–274.
Romero et al., Biochem Journal, vol. 321, No. 2, pp. 289–295.
Lussier et al., J.Cell Biology, vol. 271, No. 18, pp. 11001–11008.
Lussier et al., J.Cell Biology, vol. 131, No. 4, pp. 913–927.
Verostek et al., Glycobiology, vol. 5, No. 7, pp. 671–681.
Lussier et al., Yeast, vol. 9, No. 10, pp. 1057–1063.

*Primary Examiner*—Robert A. Schwartzman
*Assistant Examiner*—Andrea Ousley
*Attorney, Agent, or Firm*—Swabey Ogilvy Renault; France Côté

[57] ABSTRACT

The present invention relates to an antifungal in vitro and in vivo screening assays for identifying compounds which inhibit mannosyltransferases involved in protein O- and N-glycosylation. The antifungal screening assay for identifying a compound which inhibit mannosyltransferases involved in protein O- and N-glycosylation, comprises the steps of: a) subjecting proteins to a specific mannosyltransferase protein encoded by a Saccharomyces cerevisiae mannosyltransferase encoding gene, wherein said gene is selected from the group consisting of KRE2/MNT1, YUR1, KTR1, KTR2, KTR3, KTR4, KTR5, KTR6 and KTR7; b) subjecting step a) to a screened compound and determining the absence or presence of protein O- and N-glycosylation, wherein the absence of protein O- and N-glycosylation is indicative of an antifungal compound. There is also disclosed an in vitro method for the diagnosis of diseases caused by fungal infection in a patient.

8 Claims, 1 Drawing Sheet

Relational homology tree of mannosyltranferase catalytic domains of the Ktrp family

SCREENING USING S. CEREVISIAE MANNOSYLTRANSFERASE ENCODING GENES

This application is a continuation of PCT/CA99/00227 filed Mar. 16, 1999 designating the United States and claiming priority of Canadian Patent Application Serial Number 2,232,536 filed Mar. 19, 1998.

BACKGROUND OF THE INVENTION (a) Field of the Invention

The invention relates to the use of *Saccharomyces cerevisiae* highly related mannosyltransferases encoding genes that, when inhibited, cause lethality of the yeast cell and to a novel cell-based antifungal screening assay.

(b) Description of Prior Art

Fungi constitute a vital part of our ecosystem but once they penetrate the human body and start spreading they cause an infection or "mycosis" and they can pose a serious threat to human health. Fungal infections have dramatically increased in the last two (2) decades with the development of more sophisticated medical interventions and are becoming a significant cause of morbidity and mortality. Infections due to pathogenic fungi are frequently acquired by debilitated patients with depressed cell-mediated immunity such as those with HIV and now also constitute a common complication of many medical and surgical therapies. Risk factors that predispose individuals to the development of mycosis include neutropenia, use of immunosuppressive agents at the time of organ transplants, intensive chemotherapy and irradiation for hematopoietic malignancies or solid tumors, use of corticosteroids, extensive surgery and prosthetic devices, indwelling venous catheters, hyperalimentation and intravenous drug use, and when the delicate balance of the normal flora is altered through antimicrobial therapy.

The yeast genus Candida constitutes one of the major groups that cause systemic fungal infections and the five medically relevant species which are most often recovered from patients are *C. albicans, C. tropicalis, C. glabrata, C. parapsilosis* and *C. krusei*.

Much of the structure of fungal and animal cells along with their physiology and metabolism is highly conserved. This conservation in cellular function has made it difficult to find agents that selectively discriminate between pathogenic fungi and their human hosts, in the way that antibiotics do between bacteria and man. Because of this, the common antifungal drugs, like amphotericin B and the azole-based compounds are often of limited efficacy and are frequently highly toxic. In spite of these drawbacks, early initiation of antifungal therapy is crucial in increasing the survival rate of patients with disseminated candidiasis. Moreover, resistance to antifungal drugs is becoming more and more prominent. For example, 6 years after the introduction of fluconazole, an alarming proportion of Candida strains isolated from infected patients have been found to be resistant to this drug and this is especially the case with vaginal infections. There is thus, a real and urgent need for specific antifungal drugs to treat mycosis.

The fungal cell wall: a resource for new antifungal targets

In recent years, we have focused our attention on the fungal extracellular matrix, where the cell wall constitutes an essential, fungi-specific organelle that is absent from human/mammalian cells, and hence offers an excellent potential target for specific antifungal antibiotics. The cell wall of fungi is essential not only in maintaining the osmotic integrity of the fungal cell but also in cell growth, division and morphology. The cell wall contains a range of polysaccharide polymers, including chitin, $\beta$-glucans and O-Serine/Threonine-linked mannose sidechains of glycoproteins. $\beta$-glucans, homopolymers of glucose, are the main structural component of yeast cell wall, and constitute up to 60% of the dry weight of the cell wall. Based on their chemical linkage, two different types of polymers can be found: $\beta 1,3$-glucan and $\beta 1,6$-glucan.

Mannoproteins are an intrinsic part of the cell wall where they are intercalated in the meshwork of the glucose and chitin polymers and the attachment of mannose to cell surface proteins is a process essential for fungal viability. A great variety of cell surface mannoproteins are cross-linked through disulfide bounds or linked to cell wall polymers through glycosidic bonds. Many of these cell wall glycoproteins are of unknown function and do not appear to possess any enzymatic activity, but likely have structural roles in cell wall architecture and integrity.

It would be highly desirable to be provided with the identification and subsequent validation of new cell wall related targets that can be used in specific enzymatic and cellular assays leading to the discovery of new clinically useful antifungal compounds.

SUMMARY OF THE INVENTION

One aim of the present invention is to provide the identification and subsequent validation of a new target that can be used in specific enzymatic and cellular assays leading to the discovery of new clinically useful antifungal compounds.

In the yeast *Saccharomyces cerevisiae*, we have identified highly related mannosyltransferases encoding genes that, when inhibited, cause lethality of the yeast cell. These enzymes are not found in human cells as they participate in the synthesis of fungal-specific structures (O- and N- mannosyl chains in the cell wall).

The essential nature of these enzymes will serve as the basis of different screens for novel antifungal compounds.

The yeast *Saccharomyces cerevisiae*, although not a pathogen, is the proven model organism for pathogenic fungi as it is closely related taxonomically to the opportunistic pathogens and genes highly homologous to the different members of the *S. cerevisiae* mannosyltransferase family have been found in *Candida albicans*.

It can be presumed that these mannosyl transferases are also essential in C. albicans.

In accordance with the present invention there is provided antifungal screening assays for identifying compounds which inhibit mannosyltransferases involved in protein O- and N-glycosylation, which comprises the steps of:

a) subjecting specific mannosyltransferase protein encoded by a *Saccharomyces cerevisiae* mannosyltransferase encoding gene, wherein said gene is selected from the group consisting of KRE2/MNT1, YUR1, KTR1, KTR2, KTR3, KTR4, KTR5, KTR6 and KTR7;

b) subjecting step a) to a screened compound and determining absence or presence on proteins of specific O- and N-linked oligosaccharides, wherein absence of these glycans is indicative of an antifungal compound.

In accordance with the present invention there is also provided an in vivo antifungal screening assay for identifying compounds which inhibit mannosyltransferase involved in protein O- and N-glycosylation, which comprises the steps of:

a) separately cultivating a mutant yeast strain lacking at least one gene for synthesis of mannosyltransferase and a control yeast strain containing said at least one gene;

b) subjecting said both yeast strains of step a) to screened compound and determining if said compound selectively inhibits growth of a wild type strain which is indicative of an antifungal compound.

The gene used in accordance with this method may be selected from the group consisting of KRE2/MNT1, YUR1, KTR1, KTR2, KTR3, KTR4, KTR5, KTR6 and KTR7.

The mutants with defects (null or defective alleles) in one or more of the KTR genes can be examined for altered patterns of transcription of all yeast genes, by hybridizing to whole yeast genome array. These altered patterns of gene transcripts when compared to the wild type strain can be used to generate a profile or fingerprinting of the defects caused by the KTR mutations. This fingerprinting can be used to generate a diagnostic set of reporter genes regulated by the promoter and upstream elements of the relevant regulated genes. This diagnostic set of reporter genes can then be placed into yeast strains and subjected to inhibitory compounds to form a screen for compounds that elicit a reporter response equivalent to that generated by KTR defects in the mutant strains. Such compounds are candidates for inhibitors of the Ktrp proteins and hence candidates for specific antifungal inhibitors.

In accordance with the present invention there is also provided an in vivo antifungal screening assay for identifying compounds that elicit a reporter response equivalent to that generated by KTR defects in the mutant strains, which comprises the steps of:

a) cultivating yeast strains having a diagnostic set of reporter genes of defects caused by KTR mutations; and b) subjecting said yeast strains of step a) to screened compound and determining if said compound selectively inhibit growth of wild type strain which is indicative of a compound being a candidate for inhibitors of the Ktrp proteins and/or a candidate for specific antifungal inhibitors.

In accordance with the present invention there is also provided an in vitro method for the diagnosis of diseases caused by fungal infection in a patient, which comprises the steps of:

a) obtaining a biological sample from said patient;

b) subjecting said sample to PCR using a primer pair specific for a mannosyltransferase gene of *Candida albicans* homolog to a gene selected from the group consisting of KRE2/MNT1, YUR1, KTR1, KTR2, KTR3, KTR4, KTR5, KTR6 and KTR7, wherein a presence of said gene is indicative of the presence of fungal infection, such as a fungal infection caused by Candida.

In accordance with the present invention there is also provided an in vitro method for the diagnosis of diseases caused by fungal infection in a patient, which comprises the steps of:

a) obtaining a biological sample from said patient;

b) subjecting said sample to an antibody specific for a specific Ktrp mannosyltransferase antigen, wherein a presence of said antigen is indicative of the presence of fungal infection, such as a fungal infection caused by Candida.

In accordance with the present invention there is also provided the use of at least one of the *Saccharomyces cerevisiae* mannosyltransferase gene selected from the group consisting of KRE2/HNT1, YUR1, KTR1, KTR2, KTR3, KTR4, KTR5, KTR6 and KTR7 and fragments thereof as a probe for the isolation of homologs in other species.

DETAILED DESCRIPTION OF THE INVENTION

Figure 1:
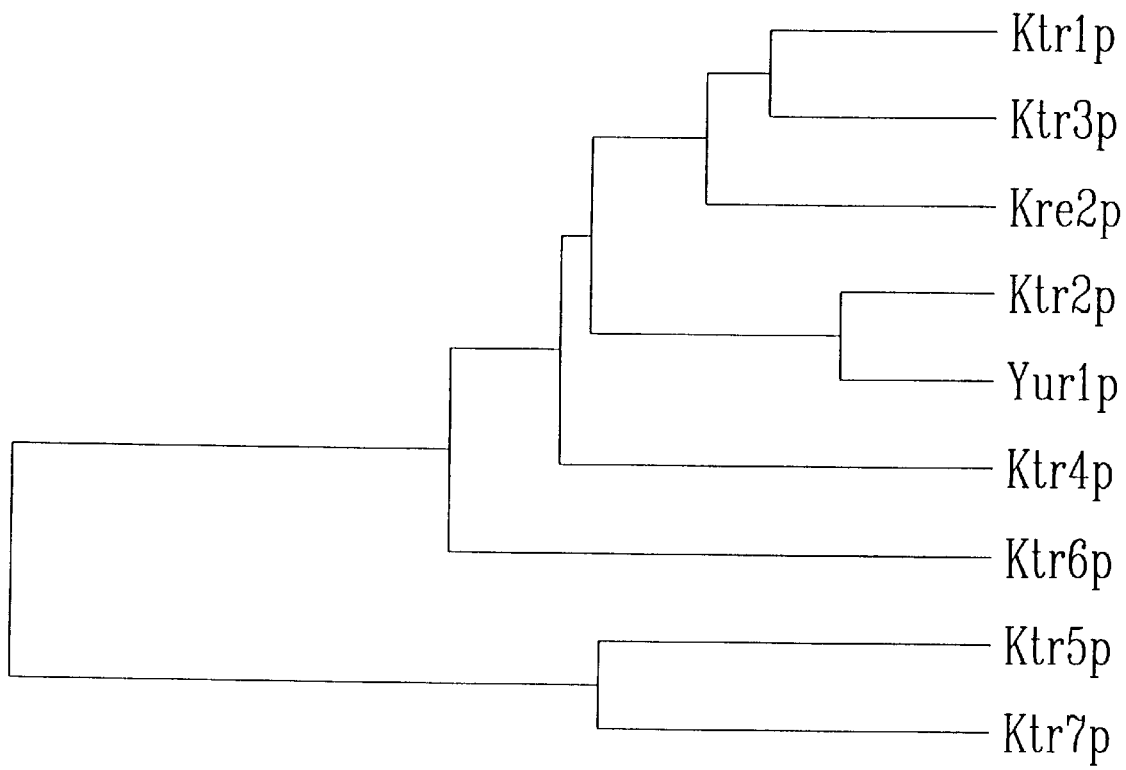
FIG. 1 illustrates the relational homology tree of mannosyltransferase catalytic domains of the Ktrp family.

In the Bussey laboratory at McGill, we work on several aspects of cell wall and glycoprotein synthesis. These studies have lead to the identification and subsequent validation of new targets that can be used in specific enzymatic and cellular assays leading to the discovery of new clinically useful antifungal compounds.

We have been studying at length the nine-membered KTR mannosyltransferase gene family of which some members have been shown to encode enzymes that are involved in the elaboration of O- and N-linked oligosaccharides of extracellular matrix proteins including those of the cell wall. The yeast complete genome sequence has revealed that the KTR gene family consists of the KRE2/MNT1, YUR1, KTR1, KTR2, KTR3, KTR4, KTR5, KTR6 and KTR7 genes (Lussier, M. et al., *Yeast* 13:267–274, 1997). As with other known glycosyltransferases, all genes in this family are predicted, and some have been shown, to encode type-II membrane proteins with a short cytoplasmic N-terminus, a membrane-spanning region, and a highly conserved catalytic lumenal domain.

Similarity between different family members is variable and ranges from 62% identity between Yur1p and Ktr2p to 24% identity for Ktr5p and Ktr6p which constitute the 2 most divergent enzymes in the family. A relational homology tree constructed using the catalytic domains of all proteins of the family has allowed grouping of the different enzymes (FIG. 1). The tree shows for example that Kre2p is most related to Ktr1p and Ktr3p, that Yur1p and Ktr2p form a subfamily as do Ktr5p and Ktr7p. In contrast, Ktr4p and Ktr6p are not closely related to each other or to any other members of the family and may play distinct roles.

The KRE2/MNT1 gene was the first member of the family to be isolated as a gene implicated in cell wall assembly conferring K1 killer toxin resistance when mutated and found to encode a medial Golgi $\alpha 1,\alpha 2$-mannosyltransferase. Kre2p/Mnt1p along with Ktr1p and Ktr3p have overlapping roles and collectively add most of the second and the third $\alpha 1,2$-linked mannose residues on O-linked oligosaccharides and are also jointly involved in N-linked glycosylation, possibly in establishing some of the outer chain $\alpha 1,2$-linkages (Lussier, M. et al., *J. Biol. Chem.* 272:15527–15531, 1997). Initial functional characterization of Yur1p and Ktr2p has revealed that they are Golgi mannosyltransferases involved in N-linked glycosylation, possibly as redundant enzymes but when inactivated show no defects in O-linked glycosylation (Lussier, M. et al., *J. of Biol. Chem.*, 271:11001.–11008, 1996. Finally, it has been recently shown that KTR6/MNN6 encodes a phosphomannosyltransferase modifying N-linked outer chains.

Multiple disruptions of KTR family members cause lethality

To explore functional relationships between the different family members of the upper branches of the relational homology tree (FIG. 1) and more closely so examine their role and essentiality, yeast strains bearing mutations in the KTR1, KTR3, KRE2, YUR1 and KTR2 genes were investigated for lethality.

Experimental strategy:

Lethality of a ktr1 ktr3 yur1 ktr2 quadruple disruptant was demonstrated by crossing both ktr1::LYS2 ktr2::URA3 ktr3::HIS3 (Mata) and ktr1::LYS2 ktr2::URA3 yur1::HIS3 (Mat ) triple disruptants, sporulating the resulting diploid and analyzing the independent assortment of the ktr3::HIS3 and yur1::HIS3 alleles in the spore progeny. All resulting spores carry inactivated copies of their KTR1 and KTR2 gene (ktrl::LYS2 ktr2::URA3).

TABLE 1

The three classes of tetrads produced in the cross

| Parental Ditype | Non Parental Ditype | Tetratype |
| --- | --- | --- |
| 2 spores: yur1::HIS3 KTR3 | 2 spores: yur1::HIS3 ktr3::HIS3 (ABSENT) | 1 spore: YUR1 KTR3 |
| 2 spores: ktr3::HIS3 YUR1 | 2 spores: YUR1 KTR3 | 1 spore: yur1::HIS3 KTR3 |
| | | 1 spore: ktr3::HIS3 YUR1 |
| | | 1 spore: yur1::HIS3 ktr3::HIS3 (ABSENT) |
| 6 tetrads of this type in total. All 4 spores are viable and His$^+$ | 7 tetrads of this type in total. 2:2 lethality. The 2 living spores are His$^-$ | 28 tetrads of this type in total. Of the 3 viable spores, 2 are His$^+$ |

Results

Deletional disruptions of the KTR1, KTR3, KRE2, YUR1 and KTR2 genes were previously obtained, and no single, double or triple disruptants were found to be lethal whereas a strain in which all five genes of this subfamily were inactivated was found to not be able to grow. A remaining question was to see whether any of the four possible quadruple disruptants resulting from different permutation of knockouts would cause death. Using standard genetic techniques ktr1 kre2 yur1 ktr2, ktr3 kre2 yur1 ktr2, ktr1 ktr3 kre2 yur1 quadruple disruptants were obtained and thus shown to be viable while a ktr1 ktr3 yur1 ktr2 disruptant could not be obtained, demonstrating the essential nature of these 4 enzymes (Table 1).

Discussion

Studying the roles of the KTR gene family has proven informative both for the analysis of the enzymes that are involved in protein O- and N-glycosylation, and also to offer insights into the biological reasons that allow such diversity of related gene products to occur. The minimal combination of genes that when inactivated cause lethality represents the 2 most homologous gene pair in the family. When only one of these 4 genes, namely KTR1, KTR2, KTR3 or YUR1, has not been inactivated in the collection of all possible quadruple disruptions, the yeast cell grows slowly suggesting that when both members of one gene pair are missing, members of the other subfamily may be partially able to functionally substitute for the missing enzymes or that inactivation of gene pairs cause different cellular defects and it is a combination of these that cause lethality.

The precise reasons why the ktr1 ktr3 yur1 ktr2 quadruple disruptant is unable to survive remain to be determined but these results again corroborate that glycosylation is an essential process in yeast. The fact that the lethality of the quadruple knock out can be moderately circumvented by growth on the osmotic stabilizer sorbitol suggest that some cell wall defects are at the source of the lethality in normal growth conditions.

Finally, these results indicate that the enzymes situated in the upper part of the relational homology tree form a functional subfamily that have highly similar roles which are very distinct from those enzymes situated in the bottom part of the tree since the presence in the genome of active copies of KTR4, KTR5, KTR6 and KTR7 cannot rescue the quadruple disruptant from death. The highly related Ktr1p, Ktr2p, Ktr3p and Yur1p enzymes can thus serve as the basis of an enzymatic screen for novel antifungal drugs since the similarity in their functioning imply that a specific compound could inhibit all of them at once and consequently kill the yeast cells.

The present invention will be more readily understood by referring to the following examples which are given to illustrate the invention rather than to limit its scope.

EXAMPLE I

In Vitro Screening Method for Specific Antifungal Agents (Enzymatic-Based Assay)

The broad aim is to identify novel compounds that inhibit the $\alpha$1,2-mannosyltransferase activities that are singly or collectively shared by Ktr1p, Ktr3p, Yur1p and Ktr2p. This task can be accomplished by existing methodologies such as the production of large amounts of each protein and by the availability of genetic tools, such as the ability to delete or overexpress gene products involved in protein glycosylation. Such assays will permit the screening of possible compounds that inhibit specific steps in the synthesis of O- and N-linked oligosaccharides, resulting in lethality or diminished virulence of the yeast cell. When such inhibitors are found, they can be evaluated as candidates for specific antifungal agents.

EXAMPLE II

Use of Ktr1p, Ktr3p, Yur1p and Ktr2p in an In Vivo Screening Method for Specific Antifungal Agents (Cellular-Based Assay)

Antifungal drug screens based on whole-cell assays in which members of the KTR family would be targeted. For example, a quadruple null mutant containing a specific Ktrp Candida albicans homolog or a KTR S. cerevisiae thermosensitive allele can be constructed permitting a specific screen in which compounds could be tested for their ability to inhibit growth or kill such a strain while having no effect on a control strain. The direct scoring on cells of the level of efficacy of a particular compound alleviates the costly and labor intensive establishment of an in vitro enzymatic assay. The availability of genetic tools, such as the ability to delete or overexpress the identified gene products permits the establishment of this new screening method. When such inhibitors are found, they can be evaluated as candidates for specific antifungal agents.

EXAMPLE III

Use of the Essential Nature of the KTR Family in All Fungi

Isolation and use of functional homologs of Ktr1p, Ktr3p, Yur1p and Ktr2p family members from all fungi. All known fungi possess mannoproteins and likely have KTR homologs in their genomes. Specific ktr mutants allow isolation of similar genes from other pathogenic fungi by functional complementation. All KTR genes can also serve as probes to isolate by homology KTR homologs from other yeasts. In addition, Ktrp allows isolation of homologs in other species by the techniques of reverse genetics where antibodies raised against any Ktrp family members could be used to screen expression libraries of pathogenic fungi for expression of KTR homologs that would immunologically cross react with antibodies raised against *S. cerevisiae* KRE2, YUR1, KTR1-7.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An antifungal screening assay for identifying compounds that inhibit mannosyltransferases involved in protein O- and N-linked glycosylation, which comprises the steps of:
   a) providing a mannosyltransferase protein encoded by a *Saccharomyces cerevisiae* mannosyltransferase encoding gene selected from the group consisting of KRE2/MNT1, YUR1, KTR1, KTR2, KTR3, KTR4, KTR5, KTR6 and KTR7 and further providing a specific substrate of said mannosvltransferase protein;
   b) subjecting the mannosyltransferase protein and specific substrate of step a) to a compound suspected of having antifungal activity and determining absence or presence on said substrate of specific O- and N-linked oligosaccharides, wherein absence of at least one of said oligosaccharides is indicative of an antifungal compound that specifically inhibits at least one member of the group of step a).

2. An in vivo antifungal screening assay for identifying compounds that inhibit mannosyltranferases involved in protein O- and N-linked glycosylation, which comprises the steps of:
   a) separately cultivating a mutant yeast strain containing at least one gene encoding a mannosyltransferase wherein said gene has been inactivated and a control yeast strain containing said at least one gene;
   b) subjecting said both yeast strains of step a) to a compound suspected of having antifungal activity; and
   c) determining if said compound selectively inhibits growth of said control yeast strain but not of said mutant yeast strain, wherein the selective inhibition of growth is indicative of an antifungal compound that inhibits a mannosyltransferase involved in protein O- and N-linked glycosylation.

3. The method of claim 2, wherein said gene is selected from the group consisting of KRE2/MNT1, YUR1, KTR1, KTR2, KTR3, KTR4, KTR5, KTR6 and KTR7.

4. An in vivo antifungal screening assay for identifying compounds that elicit a reporter gene response in yeast equivalent to that generated by yeast strains carrying a defect in a Ktrp mannosyltranferase, which comprises the steps of:
   a) cultivating a yeast strain having a diagnostic set of reporter genes for a Ktrp mannosyltransferase defect caused by a mutation in the gene encoding said mannosyltransferase;
   b) subjecting said yeast strain of step a) to a compound suspected of having antifungal activity and determining if said compound selectively elicits a response from said reporter genes equivalent to that generated by yeast strains carrying a defect in a Ktrp mannosyltranferase, wherein said response is indicative of a compound being a candidate for a specific antifungal inhibitor.

5. An in vitro method for the diagnosis of diseases caused by fungal infection in a patient, which com- prises the steps of:
   a) obtaining a biological sample from said patient;
   b) subjecting said sample to PCR using a primer pair specific for a mannosyltransferase gene of *Candida albicans* homolog to a gene selected from the group consisting of KRE2/1MNT1, YUR1, KTR1, KTR2, KTR3, KTR4, KTR5, KTR6 and KTR7, wherein a presence of said gene is indicative of the presence of fungal infection.

6. The method of claim 5, wherein said fungal infection is caused by Candida.

7. An in vitro method for the diagnosis of diseases caused by fungal infection in a patient, which comprises the steps of:
   a) obtaining a biological sample from said patient;
   b) subjecting said sample to an antibody specific for a specific Ktrp mannosyltransferase antigen, wherein a presence of said antigen is indicative of the presence of fungal infection.

8. The method of claim 7, wherein said fungal infection is caused by Candida.

* * * * *